United States Patent [19]
Vaughn et al.

[11] Patent Number: 5,530,095
[45] Date of Patent: Jun. 25, 1996

[54] PEPTIDES OF MELANIN CONCENTRATING HORMONE PRECURSOR

[75] Inventors: Joan Vaughn, San Diego; Wolfgang H. Fischer, Solano Beach; Jean E. F. Rivier, La Jolla; Jean-Louis M. Nahon; Francoise G. Presse, both of San Diego; Wylie W. Vale, Jr., La Jolla, all of Calif.

[73] Assignee: The Salk Institute for Biological Studies, La Jolla, Calif.

[21] Appl. No.: 447,613

[22] Filed: May 23, 1995

Related U.S. Application Data

[62] Division of Ser. No. 208,531, Mar. 9, 1994, Pat. No. 5,449,766, which is a division of Ser. No. 733,660, Jul. 22, 1991, abandoned, which is a division of Ser. No. 326,984, Mar. 22, 1989, Pat. No. 5,049,655.

[51] Int. Cl.$^6$ .............................. C07K 7/08; C12P 21/02
[52] U.S. Cl. ......................... 530/326; 530/327; 530/395; 435/69.4
[58] Field of Search ................................. 530/326, 327, 530/395; 435/69.4

[56] References Cited

PUBLICATIONS

Zamir et al., Proc. Natl. Acad. Sci., vol. 83, pp 1528–1531, 1986.
Breton et al., Mol. Brain Res., vol. 18, pp 297–310, 1993.
Vaughan et al., Endocrinology, vol. 125, pp. 1660–1665, 1989.

*Primary Examiner*—Garnette D. Draper
*Assistant Examiner*—Sally P. Teng
*Attorney, Agent, or Firm*—Fitch, Even, Tabin & Flannery

[57] ABSTRACT

Mammalian melanin-concentrating hormone (MCH) is isolated from rat tissue, purified and characterized. These MCH peptides are useful for treating skin disorders, for suppressing the proliferation of skin tumor cells, such as melanomas in mammals, and for modulating the secretion of ACTH. Generally, peptides are provided which have the following formula:

H—Asp—Phe—
Asp—Met—Leu—Arg—Cys—Met—Leu—Gly—Arg—Val—
Tyr—Arg—Pro—Cys—Trp—Gln—Val—OH, or which are naturally occurring homologs of the peptide with said formula. The peptides which are the naturally occurring MCH homologs of mammalian species other than rat can also be obtained using the materials disclosed, as demonstrated specifically with human MCH, which is found to have the same structure as rat MCH. Also disclosed are the amino acid sequences of, and the nucleotide sequences of the cDNAs which encode, the putative precursors of rat MCH and human MCH. These precursors may also include one or more biologically active peptides N-terminally of the mature MCH's. Among these peptides, which are thought to be formed from the MCH precursors, are the peptide with the sequence H-Glu-Ile-Gly-Asp-Glu-Glu-Asn-Ser-Ala-Lys-Phe-Pro-Ile-NH$_2$, which is cross-reactive with antibodies against alpha-MSH and CRF, and the peptide with the sequence H-Gly-X$_{NGE}$-Phe-Pro-Ala-Glu-Asn-Gly-Val-Gln-Asn-Thr-Glu-Ser-Thr-Gln-Glu-OH, wherein X$_{NGE}$ is Pro-Ala-Val or Ser-Val-Ala, which is cross-reactive with antibodies against GRF.

4 Claims, No Drawings

PEPTIDES OF MELANIN CONCENTRATING HORMONE PRECURSOR

This invention was made with Government support under Grants DK-26741 and HD-13527 awarded by the National Institutes of Health. The Government has certain rights in the invention.

This is a division of application Ser. No. 08/208,531, filed Mar. 9, 1994 now U.S. Pat. No. 5,449,766, which is a division of application Ser. No. 07/733,660, filed on Jul. 22, 1991, abandoned, which is a division of application Ser. No. 07/326,984, filed on Mar. 22, 1989, now U.S. Pat. No. 5,049,655.

This invention relates to hormones for concentrating melanin in mammals and to methods of treating mammals using such hormones.

BACKGROUND OF THE INVENTION

A cyclic heptadecapeptide which induces melanosome aggregation within fish melanophores was isolated from salmon pituitary glands, see Kawauchi, H. et al., *Nature*, 305, 321–323 (1983), and it was named melanin concentrating hormone (MCH). Fish MCH has been reported to have the opposite effect, i.e., causing dispersal of melanosomes, in amphibians, Wilkes, B. C. et al., *B.B.R.C.*, 122, 613–619 (1984). MCH is believed to be synthesized in the neurons of the hypothalamus and translocated into the neurohypophysial tissues. MCH immunoactivity has been reported in hypothalamic extracts of the rat: Baker et al., *Gen. Comp. Endocrinol.*, 50, 423–431 (1983) and Naito, N. et al., *Cell Tissue Res.*, 253, 291–295 (1988). Very crude extracts of an MCH-like substance from the rat hypothalamus showed a generally parallel response to fish MCH in a radioimmunoassay (RIA) using an antiserum directed against salmon MCH, even though the material appeared to have distinct chromatographic properties and showed multiple immunoreactive peaks, not all of which showed bioactivity, Zamir, N. et al., *P.N.A.S. USA*, 83, 1428–1531 (1986); Sekiya, K. et al., *Neuroscience*, 25, 925–930 (1988); Naito, N. et al., (1988) supra.

Despite all of this work over a period of several years, the mammalian hormone remains unisolated and uncharacterized, and as a result, true testing of the biological activity of mammalian MCH has not heretofore been possible. As a result, great efforts were made to isolate, purify and then characterize and test mammalian MCH.

SUMMARY OF THE INVENTION

A mammalian MCH has now been isolated and purified from rat hypothalamus. Characterization of the purified peptide shows that it is 19 amino acid residues in length and in cyclic form.

By the preparation of DNA probes based upon the characterized sequence of the peptide, it was possible to locate cDNAs coding for mammalian MCH from libraries made using rat and human hypothalamic messenger RNA. By isolating the cDNAs from the positive clones (i.e., those identified with the DNA probes as harboring desired cDNAs) of the libraries, it was possible to obtain the sequences of the cDNAs and, by reading the sequences, confirm the precise sequence for the mature peptide of the rat, determine the precise sequence for the mature peptide of the human, and also deduce the sequences for the precursor peptides that are apparently originally expressed from the gene in the rat and human cells of interest prior to (or simultaneously with) processing to yield the mature peptides. Further, as a result of the isolation and then sequencing of the cDNA's, which were made possible by the isolation and sequencing of the mature rat peptide, it was possible to determine that the C-terminus of the native MCH peptide is in the free acid form.

The amino acid sequences of the mature MCH's of rat and human, as determined by the sequencing of the mature rat peptide and deduced from the sequences of the cDNA segments encoding the hormones, are identical. Further, of the 54 base pairs in these DNA segments, differences in sequence occur at only three positions. The identity of amino acid sequences and close homology in cDNA sequences indicate that all mammalian mature MCH's have sequences that are closely similar.

Further, from the sequencing of the cDNAs encoding the MCH precursors, it has been found that there is very close homology between the cDNA sequences and the corresponding amino acid sequences. Indeed, both the rat and the human precursors have the same number of amino acids, 165.

Inasmuch as it appears that there is very close homology between the mature MCHs, MCH precursors, and mRNAs enoding these proteins of mammalian species, it is believed that the DNA probes which are based upon the actual rat mature MCH peptide sequence (or other sequences provided herein using probes based on that rat peptide sequence) will be effective in identifying clones with MCH-encoding or MCH precursor-encoding cDNAs in libraries made with mRNAs obtained from appropriate tissue (e.g., hypothalamus) or cell lines of other mammalian species and thus will permit the determination of the sequences, and consequently the synthesis and use, of the mature MCH of every mammalian species.

Among the mammalian MCH's, the present invention is especially concerned with the mature MCH having the following structure:

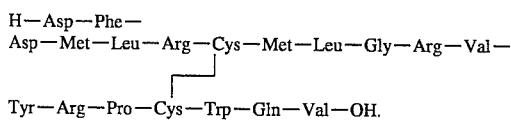

Reference in the present application to a "mammalian MCH" is to a mammalian mature MCH, unless the term is explicitly qualified to refer to a mammalian MCH precursor.

Mammalian MCH is useful to treat humans and other mammals to lighten skin color, as by local or topical application. It is also useful to suppress the proliferation of certain skin tumor cells, such as melanomas, when suitably applied as by topical application or the like. It is also found that mammalian MCH can be used to modulate the secretion of ACTH in humans and other mammals and thus can be used to modify the effects of stress, as by systemically administering an effective amount of mammalian MCH.

The invention also comprehends a mammalian peptide, designated "NEI," for "neuropeptide N-terminal E C-terminal I" (E being the abbreviation for glutamic acid and I being the abbreviation for isoleucine), which has as its sequence Glu-Ile-Gly-Asp-Glu-Glu-Asn-Ser-Ala-Lys-Phe-Pro-Ile-NH$_2$. A mammalian NEI is apparently made in vivo in a mammal by processing beginning with the MCH precursor of the mammal. The sequences of all mammalian NEI's are closely similar, as indicated by the fact that the amino acid sequences of the rat and human NEI's are identical.

The invention also includes the peptides, designated "NGE," for "neuropeptide N-terminal G C-terminal E" (G being the abbreviation for glycine and E being the abbreviation for glutamic acid), which have as their sequences Gly-$X_{NGE}$-Phe-Pro-Ala-Glu-Asn-Gly-Val-Gln-Asn-Thr-Glu-Ser-Thr-Gln-Glu, wherein $X_{NGE}$ is Pro-Ala-Val (as in rat NGE) or Ser-Val-Ala (as in human NGE). Like NEI, a mammalian NGE is apparently also made in vivo in a mammal by processing beginning with the MCH precursor of the mammal. Further, the sequences of all mammalian NGE's are closely similar, as indicated by the fact that the amino acid sequences of the rat and human NGE's differ at only three of 19 amino acids, with two of the three differences being conservative.

The sequence of NEI corresponds to the sequence of amino acids 131–144 of the rat and human MCH precursors (see Tables 1 and 2, below), taking account of the fact that the glycine at position 144 of the MCH precursors would provide the $NH_2$ group of the C-terminal amide of NEI. It has been found that antibodies against human alpha-MSH (i.e., alpha-melanocyte stimulating hormone) and human CRF (corticotropin-releasing factor) cross-react with NEI, with the anti-alpha-MSH antibodies recognizing an epitope including the N-terminus of NEI and the anti-CRF antibodies recognizing an epitope including the C-terminus of NEI. It is thought that NEI has a biological function in vivo.

The sequences of the NGE's correspond to the sequences of amino acids 110–128 of the MCH precursors (see Tables 1 and 2, below). Antibodies against human GRF (growth hormone releasing factor) cross-react with NGE, as suggested by our discovery of the close homology between the sequence Gln-Gln-Gly-Glu-Ser-Asn-Gln-Glu of amino acids 30–37 of human GRF and amino acids 12–19 of the NGE's. It is thought that NGE's, like NEI, have a biological function in vivo.

NEI is useful, in the process of making anti-alpha-MSH or anti-CRF monoclonal antibody-secreting hybridomas, as an immunogen for obtaining anti-alpha-MSH or anti-CRF antibody-producing splenocytes or lymphocytes and as an antigen for screening cultures of hybridomas for those which include hybridomas that make anti-MSH or anti-CRF antibodies. Similarly, NGE is useful in the process of making anti-GRF monoclonal antibody-secreting hybridomas. Monoclonal antibodies wade by such hybridomas are useful for assaying for alpha-MSH, CRF or GRF by standard immunoassay methods.

Further, such a monoclonal antibody wade with NEI or NGE as the immunogen, when used in a standard immunoaassay procedure in conjunction with a second monoclonal antibody, which recognizes an epitope of alpha-MSH, CRF or GRF different from the epitope recognized by the monoclonal antibody made with NEI or NGE as the immunogen, can be used to confirm that a peptide detected in an immunoassay is alpha-MSH, CRF or GRF rather than NEI, NGE or some other peptide that shares the epitope common between NEI and alpha-MSH, NEI and CRF, or NGE and GRF. Such a confirmatory assay would be useful, for example, in assaying tumor cells, from a patient thought to be suffering from a cancer involving aberrant expression of alpha-MSH, CRF or GRF, to ascertain whether the cancer does in fact entail aberrant expression of one of those hormones or entails instead aberrant expression of NEI, NGE or some other peptide.

DETAILED DESCRIPTION OF THE INVENTION

Mammalian melanin-concentrating hormone (MCH) has now been isolated from rat hypothalami by acid extraction and purified substantially by immunoaffinity chromatography using antiserum directed against salmon MCH, gel filtration and two steps of narrow bore high-performance liquid chromatography (HPLC) using octadecyl columns. Several zones of immunoreactivity were isolated; however, Edman degradation in a gas-phase sequencer indicates that the amino acid structure of all zones are identical. As a result, it is believed that rat hypothalamic MCH is a cyclic peptide of 19 amino acid residues. More particularly, the invention provides peptides having the following structure:

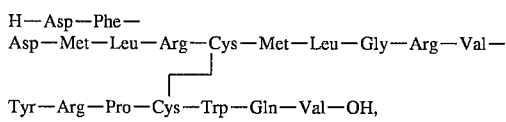

and naturally occurring homologs thereof (i.e., homologous MCH peptides of mammalian species other than rat and human (for which the structure of the MCH is identical to that of rat)).

The invention also provides the peptides having the sequence H-Glu-Ile-Gly-Asp-Glu-Glu-Asn-Ser-Ala-Lys-Phe-Pro-Ile-$NH_2$ (designated NEI), and naturally occurring homologs thereof (i.e., homologous NEI peptides of mammalian species other than rat and human (for which the structure of the NEI is identical to that of rat)); and peptides having the sequence H-Gly-$X_{NGE}$-Phe-Pro-Ala-Glu-Asn-Gly-Val-Gln-Asn-Thr-Glu-Ser-Thr-Gln-Glu-OH (designated NGE), wherein $X_{NGE}$ is Pro-Ala-Val or Ser-Val-Ala, and naturally occuring homologs thereof (i.e., homologous NGE peptides of mammalian species other than rat and human).

The invention further entails DNAs each of which comprises a segment which consists of a sequence of triplets (i.e., is a cDNA segment) and which, if expressed, would encode a polypeptide with the amino acid sequence of a peptide according to the invention or, if the peptide of the invention is C-terminally amidated, said sequence with a Gly residue added at the C-terminus. Among such DNAs are the DNA segments which consist of a sequence of triplets (i.e., sets of three base pairs) and which, if expressed, would encode a polypeptide with the amino acid sequence of a peptide according to the invention (or, if the peptide of the invention is C-terminally amidated, said sequence with a Gly residue added at the C-terminus) and those DNAs, such as expression vectors, which, upon transformation into a suitable host, are capable of being expressed to yield a peptide according to the invention.

Probing of a rat hypothalamic cDNA library made using mRNA from rat hypothalami was carried out using a synthetic oligonucleotide probe with a sequence which was based on the sequence of residues 1–10 of the above-identified, mature MCH sequence of rat. Several positive hits were obtained, and the culturing of the positive clones allowed the isolation of cDNAs encoding the entire precursor of rat MCH. With such cDNA, the nucleotide sequence coding the precursor was determined and, with the nucleotide sequence, the amino acid sequence of the precursor deduced. This work confirmed that the mature MCH peptide has the above-identified structure and is free acid at the C-terminus. Further, the work provided the information from which the sequences of NEI and NGE could be determined.

Substantially the same procedure was followed to isolate and sequence cDNAs encoding the human MCH precursor. To isolate such cDNAs, a human hypothalamic cDNA library was screened with a probe taken from a portion, encoding part of rat mature MCH, of the cDNA encoding the rat MCH precursor. Using the sequence information from the cDNAs encoding the human MCH precursor, the amino acid sequences of human mature MCH, its precursor, and human NEI and NGE were deduced.

A portion, encoding mature MCH with the dipeptide Arg-Arg, which is a proteolytic processing site, at the N-terminus, of the oligonucleotide sequence of the rat cDNA, with amino acid residues set forth immediately therebelow, is as follows:

```
AGG AGA GAT TTT GAC ATG CTC AGG TGT ATG CTG GGA CGA GTC TAC CGA CCC TGT TGG CAA GTC TGA
Arg—Arg—Asp—Phe—Asp—Met—Leu—Arg—Cys—Met—Leu—Gly—Arg—Val—Tyr—Arg—Pro—Cys—Trp—Gln—Val.
 1               5                       10                      15
```

Human mature MCH has the same amino acid sequence as that of rat and, like the rat, is preceded by the dipeptide Arg-Arg in the human MCH precursor. As indicated in Tables 1 and 2 below, the nucleotide sequence of the cDNA segment encoding human mature MCH and the Arg-Arg preceding the protein in the precursor differs at only three of 57 positions from the sequence of the cDNA indicated immediately above for the rat.

Because, based on the observation that most mammalian peptide hormones have amino acid sequences that differ little from mammalian species to mammalian species and based on the high degree of homology found in connection with the present invention between rat and human mature MCH's and MCH precursors, and the cDNAs encoding same, possession of the above-identified rat and human nucleotide sequences allows the construction of nucleic acid probes that will hybridize with cDNA fragments, coding for the mature MCH and MCH precursor, in a cDNA library of suitable tissue (e.g., the hypothalmus), or a suitable cell line, of any mammalian species, as was done in the screening of the rat and human hypothalamic cDNA libraries as described above. Thus, possession of the sequences allows deduction of the specific amino acid sequences of the mature MCH hormone and NEI and NGE of such other species. Such techniques of using a suitable hybridization probe for screening and then carrying out sequence analysis of the positive cDNA clones are well known in the molecular biology art; one example is shown in European Patent Application number 0 226 181, published Jun. 24, 1987, the disclosure of which is incorporated herein by reference.

In this respect, the following probe: 5'-CCAA-CAGGGTCGGTAGACTCGTCCCAGCAT, taken from the complementary strand of the above-specified strand of the rat cDNA sequence, was employed for probing for cDNAs encoding human MCH and its precursor and as expected, hybridized with clones of a human λgt11 cDNA library prepared with human hypthalamic mRNA.

Isolation of a cDNA coding for mammalian MCH or MCH precursor of another particular species, as has been accomplished for the rat and human species, will allow, as it has for the rat and human, the determination of the amino acid sequence of the MCH peptide, as well as of the NEI and NGE, of the species.

With the amino acid sequences of such peptides, for the human, the rat or any other mammalian species, so determined, the peptides can be made in substantially pure form using well known recombinant DNA technology, as described in more detail hereinafter and as also described in detail in the aforesaid European patent application, or, preferably, in view of the small number of amino acids in the peptides, using solid-phase or other types of chemical syntheses. Thus, the invention provides methods for producing the MCH, NEI and NGE specific to any mammalian species.

Further, the invention, by making available substantial quantities of substantially pure MCH's of mammalian species, also provides various uses of the mammalian MCH's according to the invention, including a method of lightening skin color of a mammal comprising administering thereto an effective amount of such a MCH, a method of suppressing the proliferation of skin tumor cells in a mammal comprising administering thereto an effective amount of such a MCH, and a method of suppressing the secretion of ACTH in a mammal comprising administering thereto an effective amount of such a MCH.

Although it may be preferable to synthesize peptides of about 25 residues or less in length using the well-known chain elongation techniques, such as solid-phase synthesis on a Merrifield resin or the like, such peptides may also be synthesized, and peptides with more than about 50–60 residues will be synthesized, using recombinant DNA methods. To synthesize a peptide containing only naturally occurring amino acid residues by recombinant DNA, a double-stranded DNA chain which encodes the desired amino acid sequence can be synthetically constructed. The degeneracy of the genetic code permits a wide variety of codon combinations to be used to form the DNA chain that encodes the product polypeptide. Certain particular codons are more efficient for polypeptide expression in certain types of organisms, and the selection of codons preferably is made according to those codons which are most efficient for expression in the type of organism which is to serve as the host for the recombinant vector. However, any correct set of codons should encode the desired product, even if slightly less efficiently. Codon selection may also depend upon vector construction considerations; for example, it may be necessary to avoid creating a particular restriction site in the DNA chain if, subsequent to insertion of the synthetic DNA chain, the vector is to be manipulated using a restriction enzyme that cleaves at such a site. Also, it is necessary to avoid placing restriction sites in the DNA chain if the host organism which is to be transformed with the recombinant vector containing the DNA chain is known to produce a restriction enzyme that would cleave at such a site within the DNA chain.

In addition to the sequences encoding the desired peptide, the DNA chain that is synthesized may contain additional sequences, depending upon vector construction considerations. Typically, a DNA chain is synthesized with linkers at its ends to facilitate insertion into restriction sites within an expression vector. The DNA chain may be constructed so as to encode the desired sequence as a portion of a fusion polypeptide; and if so, it will generally contain terminal sequences that encode amino acid sequences that serve as proteolytic processing sites, whereby the desired polypeptide may be proteolytically cleaved from the remainder of the fusion polypeptide. The terminal portions of the synthetic DNA chain may also contain sequences appropriate to provide transcription and translation start signals, transcription and translation stop signals, and a polyadenylation signal and site.

To assemble the desired DNA chain, oligonucleotides are constructed by conventional methods, such as procedures described in T. Manatis et al., *Cold Spring Harbor Laboratory Manual,* Cold Spring Harbor, N.Y. (1982) (hereinafter, CSH). Sense and antisense oligonucleotide chains, up to about 70 nucleotide residues long, are synthesized, preferably on automated synthesizers, such as the Applied Biosystem Inc. model 380A DNA synthesizer. The oligonucleotide chains are constructed so that portions of the sense and antisense oligonucleotides overlap, associating with each other through hydrogen bonding between complementary base pairs and thereby forming double stranded chains, in most cases with gaps in the strands. Subsequently, the gaps in the strands are filled in, and oligonucleotides of each strand are joined end to end with nucleotide triphosphates in the presence of appropriate DNA polymerases and/or with ligases.

As an alternative to construction of a synthetic DNA chain through oligonucleotide synthesis for a peptide that is a naturally occurring molecule, such as mammalian MCH or its precursor, cDNA corresponding to the desired peptide may be obtained. A cDNA library or an expression library is produced in a conventional manner by reverse transcription from messenger RNA (mRNA) from a MCH-producing cell line or cells of a tissue in which MCH is made. To select clones containing MCH sequences, hybridization probes (preferably a mixture of probes to accommodate the degeneracy of the genetic code) corresponding to portions of the MCH protein are produced and used to identify through nucleic acid probe hybridization analysis clones containing MCH-encoding sequences. If the library is an expression library, screening of the library with anti-MCH antibodies (alone or together with anti-NEI or anti-NGE antibodies) may also be used, alone or in conjunction with nucleic acid probe hybridization probing, to identify or confirm the presence of MCH-encoding or MCH-precursor-encoding DNA sequences in clones of the library. Such techniques are taught, for example in CSH, supra.

The double-stranded DNA chain of interest, whether made by chemical synthesis of oligonucleotides or by isolation from a cDNA library, is modified as necessary to permit its insertion into an expression vector operatively for expression of the desired peptide (mature MCH, NEI, NGE or MCH precursor, for example) in a host transformed with the vector. For example, if the DNA chain is to be inserted into a vector for transformation of a prokaryotic host, such as *E. coli,* the DNA chain will be inserted 3' of a promoter sequence, a sequence encoding a Shine-Delgarno sequence (or ribosome binding site) that is within a 5' non-translated portion of the RNA made by transcription of the DNA, and an ATG translation start signal (or, more accurately, a triplet of sequence 5'-ATG encoding an 5'-AUG codon to signal translational start). The ATG start signal is appropriately spaced from the Shine-Delgarno sequence, and the encoding sequence is placed in correct reading frame with respect to the ATG start codon. The expression vector also provides a translational termination codon and a 3' non-translated region. For an expression vector to be transformed into an eukaryotic host, such as a yeast or a cell line obtained from a higher animal, the DNA sequence encoding the desired peptide is appropriately spaced 3' (i.e., downstream) from a promoter, a capping site and an ATG translational start signal, in correct reading frame with respect to the ATG translation start signal, and 5' from a translation termination signal, a polyadenylation signal and site, and a transcription termination site.

Prokaryotic transformation vectors, such as pBR322, pMB9, ColE1, pCR1, RP4 and lambda-phage, are available for inserting a DNA chain of the length necessary to encode the peptide of interest with substantial assurance of at least some expression of the encoded polypeptide in a suitable transformed host. Typically, such vectors are constructed or modified to have a unique restriction site(s) appropriately positioned relative to a promoter, such as the lac promoter. The DNA chain may be inserted with appropriate linkers into such a restriction site, with substantial assurance of production of a peptide of interest in a culture of a prokaryote transformed with the recombinant vector. To assure the proper reading frame, linkers of various lengths may be provided at the ends of the sequence encoding the desired peptide. Alternatively, cassettes, which include sequences, such as the 5' region of the lac Z gene (including the operator, promoter, transcription start site, Shine Delgarno sequence and translation initiation signal), the regulatory region from the tryptophan gene (trp operator, promoter, ribosome binding site and translation initiator), and a fusion gene containing these two promoters, called the trp-lac or commonly called the Tac promoter, are available into which a synthetic DNA chain may be conveniently inserted before the cassette is inserted into an expression vector of choice.

Similarly, eukaryotic transformation vectors, such as the cloned bovine papilloma virus genome, the cloned genomes of the murine retroviruses, and eukaryotic cassettes, such as the pSV-2 gpt system (described by Mulligan and Berg, *Nature,* 277, 108–114, 1979), the Okayama-Berg cloning system (*Mol. Cell Biol.* 2, 161–170, 1982) and the expression vector described by Genetics Institute (*Science* 228, 810–815, 1985) are available which provide substantial assurance of at least some expression of the desired peptide in the transformed eukaryotic cell line.

Another way to produce peptides of desired length is to produce the peptide initially as a segment of a gene-encoded fusion polypeptide. In such case, the DNA chain is constructed so that the expressed polypeptide has enzymatic, proteolytic processing sites flanking the MCH sequence. A peptide-encoding DNA chain may be inserted, for example, into the beta-galactosidase gene for expression after transformation into *E. Coli,* in which case the expressed fusion polypeptide is subsequently cleaved with appropriate proteolytic enzymes to release the desired peptide from beta-galactosidase peptide sequences.

An advantage of inserting the sequence encoding the desired peptide so that the peptide is expressed as a cleavable segment of a fusion polypeptide, e.g., as the mature MCH sequence fused within the beta-galactosidase peptide sequence, is that the polypeptide into which the sequence for the esired peptide is inserted is generally rendered non-functional, thereby facilitating selection of transformants with vectors encoding the fusion peptide.

Purification of a desired peptide to substantial purity, i.e., at least about 95 weight percent of all protein, can be effected from a culture of a microorganism genetically engineered to express the peptide or from a mixture of polypeptides (that may result, for example, from a solid-phase chemical synthesis) by the teachings set forth hereinafter.

As previously indicated, the mature MCHs, NEIs and NGEs can be, and preferably are, synthesized by suitable chain elongation or coupling-type methods, such as by exclusively solid-phase techniques, by partial solid-phase techniques, by fragment condensation or by classical solution couplings. The techniques of exclusively solid-phase synthesis are set forth in the textbook *Solid-Phase Peptide Synthesis,* by Stewart and Young, Pierce Chemical Co., Rockford, Ill., 1984, and are exemplified by the disclosure of U.S. Pat. No. 4,105,603, issued Aug. 8, 1978. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to coupling-type syntheses is the protection of the labile side-chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Such an intermediate for an MCH peptide may have the formula:

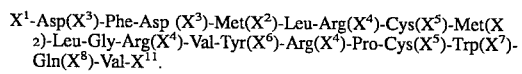

Such an intermediate for an NEI peptide may have the formula:

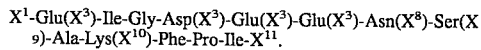

Such an intermediate for an NGE peptide may have the formula:

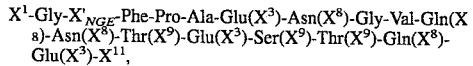

wherein $X'_{NGE}$ is Pro-Ala-Val or Ser($X^9$)-Val-Ala.

Such intermediates are also part of the instant invention.

$X^1$ is either hydrogen or an alpha-amino protecting group. The alpha-amino protecting groups contemplated by $X^1$ are those well known to be useful in the art of stepwise synthesis of polypeptides. Among the classes of alpha-amino protecting groups which may be employed as $X^1$ are (1) aromatic urethan-type protecting groups, such as fluorenylmethyloxycarbonyl (Fmoc), benzyloxycarbonyl (Z) and substituted Z, such as p-chlorobenzyloxycarbonyl, p-nitrobenzyloxycarbonyl, p-bromobenzyloxycarbonyl, and p-methoxybenzyloxycarbonyl; (2) aliphatic urethan protecting groups, such as t-butyloxycarbonyl (BOC), diisopropylmethyloxycarbonyl, isopropyloxycarbonyl, ethoxycarbonyl, allyloxycarbonyl; and (3) cycloalkyl urethan-type protecting groups, such as cyclopentyloxycarbonyl, adamantyloxycarbonyl, and cyclohexyloxycarbonyl. The preferred alpha-amino protecting group is BOC.

$X^2$ is oxygen, to protect the sulfur of methionine, or no protecting group, preferably the latter.

$X^3$ is hydrogen or a suitable ester-forming protecting group for the carboxyl group of Asp or Glu, such as benzyl(OBzl), 2,6-dichlorobenzyl, methyl and ethyl.

$X^4$ is a suitable protecting group for the guanido group of Arg, such as nitro, Tos, CBZ, adamantyloxycarbonyl, and BOC, or is hydrogen.

$X^5$ is a protecting group for the sulfhydryl group of Cys, preferably p-methoxybenzyl(MeOBzl), p-methylbenzyl, acetamidomethyl, trityl or Bzl.

$X^6$ is hydrogen or a suitable protecting group for the phenolic hydroxyl group of Tyr, such as tetrahydropyranyl, tert-butyl, trityl, Bzl, CBZ, 4Br-CBZ and 2,6-dichlorobenzyl(DCB). The preferred protecting group is 2,6-dichlorobenzyl.

$X^7$ is hydrogen or a protecting group for the indole nitrogen of Trp, such as formyl or benzyl; however, in many syntheses there is no need to protect Trp.

$X^8$ is hydrogen or a suitable protecting group, such as xanthyl (Xan) for the side chain amido group of Asn or Gln. It is preferably hydrogen.

$X^9$ is hydrogen or a protecting group for the hydroxyl group of Ser or Thr and is selected from acetyl, benzoyl, tert-butyl, trityl, tetrahydropyranyl, Bzl, 2,6-dichlorobenzyl, and CBZ. Bzl is preferred.

$X^{10}$ is hydrogen or a protecting group for the side-chain amino group of Lys and is selected from 2-chlorobenzyloxycarbonyl (2-Cl-Z), Tos, CBZ, t-amoxycarbonyl and BOC. The selection of a side chain amino protecting group is not critical except that generally one is chosen which is not removed during deprotection of the alpha-amino groups during the synthesis.

$X^{11}$ is a suitable protecting group for the C-terminal carboxyl group, such as the ester-forming group $X^3$, or is a resin support, used in solid phase synthesis, with an anchoring bond to the peptide.

When a solid resin support is used, it may be any of those known in the art, such as one wherein $X^{11}$ has the formula: —O—CH$_2$-resin support. Should it be desired to make the unsubstituted C-terminal amide, as in NEI, use of BHA ($X^{11}$: —NH-benzhydrylamine-resin support) or MBHA ($X^{11}$: —NH-paramethylbenzhydrylamine-resin support) resin support is preferred, because cleavage gives the amide directly. In case the N-methyl amide is desired, it can be generated from an N-methyl BHA resin. Should other substituted amides be desired, the teaching of U.S. Pat. No. 4,569,967 can be used. Should still other groups than the free acid or amido be desired at the C-terminus, it may be preferable to sythesize the peptide using classical solution methods, as set forth in the Houben-Weyl text (*Synthese von Peptiden*, in *Methoden der organischen Chemie*, E. Wunsch, ed., Band XV, Teilen 1 und 2, Georg Thieme Verlag, Stuttgart, FRD (1974)), or solid-phase methods, according to Stewart and Young, supra.

In the formulae for the intermediates, at least one of the X-groups is a protecting group or $X^{11}$ includes resin support.

Thus, there is also provided by the present invention a method for manufacturing an MCH by carrying out the following steps: (a) forming a peptide having at least one protecting group and the sequence of the desired MCH, wherein the protecting groups are as described above and wherein the carboxy-terminus is either protected or bound to a resin support; (b) cleaving the protecting group or groups and, if present, the bond between the peptide and the resin support; (c) either before or after step (b), forming a disulfide bond between the Cys residues, if not already formed; and (d) if desired, converting the resulting peptide into a pharmaceutically acceptable, non-toxic salt thereof.

Further, there is provided by the invention a method for manufacturing an NEI by carrying out the following steps: (a) forming a peptide having at least one protecting group and the sequence of the desired NEI, wherein the protecting groups are as described above and wherein the carboxy-terminus is bound to a BHA or MBHA resin support; (b) cleaving the protecting group or groups and the bond between the peptide amide and the resin support; and (c) if desired, converting the resulting peptide amide into a pharmaceutically acceptable, non-toxic salt thereof.

Still further, there is provided by the present invention a method for manufacturing an NGE by carrying out the following steps: (a) forming a peptide having at least one protecting group and the sequence of the desired NGE, wherein the protecting groups are as described above and wherein the carboxy-terminus is either protected or bound to a resin support; (b) cleaving the protecting group or groups and, if present, the bond between the peptide and the resin support; and (c) if desired, converting the resulting peptide into a pharmaceutically acceptable, non-toxic salt thereof.

In selecting a particular side chain protecting group to be used in the synthesis of the peptides, the following general rules are followed: (a) the protecting group preferably retains its protecting properties and is not split off under coupling conditions, (b) the protecting group should be stable to the reagent and, with the exception of Xan, is preferably stable under the reaction conditions selected for removing the alpha-amino protecting group at each step of the synthesis, and (c) the side chain protecting group must be removable, upon the completion of the synthesis containing the desired amino acid sequence, under reaction conditions that will not undesirably alter the peptide chain.

When peptides are not prepared using recombinant DNA technology, they are preferably prepared using solid phase synthesis, such as that generally described by Merrifield, *J. Am. Chem. Soc.*, 85, p 2149 (1963), although other equivalent chemical syntheses known in the art can also be used as previously mentioned, see, e.g., Stewart and Young, supra.

Solid-phase synthesis is commenced from the C-terminus of the peptide by coupling a protected alpha-amino acid to a suitable resin. Such a starting material can be prepared by attaching an alpha-amino-protected amino acid by an ester linkage to either a chloromethylated resin or a hydroxymethyl resin (particularly when the desired peptide has a free acid C-terminus), or by an amide bond to a BHA resin or MBHA resin (when the desired peptide has an unsubstituted C-terminal amide). The preparation of the hydroxymethyl resin is described by Bodansky et al., *Chem. Ind.* (London) 38, 1597–98 (1966). Chloromethylated resins are commercially available from Bio Rad Laboratories, Richmond, Calif. and from Lab. Systems, Inc. The preparation of such a resin is described by Stewart and Young, supra, Chapter 1, pp 1–9. BHA and MBHA resin supports are easily synthesized and are commercially available as well.

The C-terminal amino acid, e.g. Val, protected by BOC, can be first coupled to the chloromethylated resin according to the procedure set forth in *Chemistry Letters*, K. Horiki et al. 165–168 (1978), using KF in DMF at about 60° C. for 24 hours with stirring. Following the coupling of the BOC-protected amino acid to the resin support, the alpha-amino protecting group is removed, as by using trifluoroacetic acid(TFA) in methylene chloride or TFA alone. The deprotection is carried out at a temperature between about 0° C. and room temperature. Other standard cleaving reagents, such as HCl in dioxane, and conditions for removal of specific alpha-amino protecting groups may be used as described in Schroder & Lubke, "The Peptides", 1 pp 72–75 (Academic Press 1965).

After removal of the alpha-amino protecting group, the remaining alpha-amino- and side-chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCC).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke, supra, in Chapter III and by Kapoor, *J. Phar. Sci.*, 59, pp 1–27 (1970).

Each protected amino acid or amino acid sequence is introduced into the solid phase reactor in about a fourfold or more excess, and the coupling may be carried out in a medium of dimethylformamide(DMF): $CH_2Cl_2$ (1:1) or in DMF or $CH_2Cl_2$ alone. In cases where incomplete coupling occurs, the coupling procedure is repeated before removal of the alpha-amino protecting group prior to the coupling of the next amino acid. The success of the coupling reaction at each stage of the synthesis, if performed manually, is preferably monitored by the ninhydrin reaction, as described by E. Kaiser et al., *Anal. Biochem.* 34, 595 (1970). The coupling reactions can be performed automatically, as on a Beckman 990 automatic synthesizer, using a program such as that reported in Rivier et al. *Biopolymers*, 1978, 17, pp 1927–1938.

After the desired amino acid sequence has been completed, cyclization (i.e., disulfide bond formation between Cys residues) can then be effected or the intermediate peptide can be removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$, $X^7$ and $X^8$, $X^9$, $X^{10}$, and the resin support (and associated linker to the peptide) $X^{11}$ and also the alpha-amino protecting group $X^1$, to obtain the peptide in the form of the free acid or the amide (if BHA or MBHA resin support was employed). Because Met is present in the MCH sequence, the BOC protecting group is preferably first removed using trifluoroacetic acid(TFA)/ethanedithiol prior to cleaving the peptide from the resin with HF to eliminate potential S-alkylation. When using hydrogen fluoride for cleaving, one or more scavengers, such as anisole, cresol, dimethyl sulfide, and methylethyl sulfide are included in the reaction vessel.

Disulphide bond formation between Cys residues to cyclize a peptide is preferably effected on the peptide separated from the resin support. Thus, deprotection as well as cleavage of the peptide from the resin support is carried out at 0° C. with hydrofluoric acid (HF) in the presence of scavengers, such as anisole, as understood in the art. The cyclic form of the peptide can then be obtained by oxidizing using a ferricyanide solution, as described in Rivier et al., *Biopolymers*, Vol. 17 (1978), 1927–38, or by air oxidation, or in accordance with other known procedures.

The following Example I sets forth a preferred method for synthesizing peptides by the solid-phase technique. It will of course be appreciated that the synthesis of a correspondingly longer peptide is effected in the same manner by merely adding the requisite number of amino acids either at the C-terminus or the N-terminus of the chain.

EXAMPLE I

The synthesis of the MCH peptide having the formula:

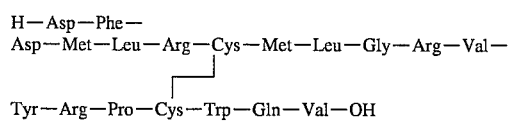

is conducted in a stepwise manner using a Beckman 990 peptide synthesizer on a commercially available chloromethylated polystyrene resin, such as LS-601 available from Lab Systems, Inc., using the technique generally described in Vale et al. U.S. Pat. No. 4,393,050. Coupling of BOC-Val to the resin results in the substitution of about 0.35 mmol. Val per gram of resin.

After deblocking and neutralization, the peptide chain is built step-by-step on the resin. Deblocking, neutralization and addition of each amino acid is performed in general accordance with the procedure set forth in detail in Rivier, J, *J. Amer. Chem. Soc.*, 96, 2986–2992 (1974). All solvents that are used are carefully degassed by sparging with an inert gas, e.g. helium or nitrogen.

Deblocking is preferably carried out in accordance with Schedule A which follows:

SCHEDULE A

| | Reagent | Mixing time (Min.) |
|---|---|---|
| 1. | 60% TFA/2% ethanedithiol | 10 |
| 2. | 60% TFA/2% ethanedithiol | 15 |
| 3. | IPA/1% ethanedithiol | 0.5 |
| 4. | $Et_3N$ (10%) in $CH_2Cl_2$ | 0.5 |
| 5. | MeOH | 0.5 |
| 6. | $Et_3N$ (10%) in $CH_2Cl_2$ | 0.5 |
| 7. | MeOH (twice) | 0.5 |
| 8. | $CH_2Cl_2$ (twice) | 0.5 |

The couplings are preferably carried out as set out in Schedule B which follows:

SCHEDULE B

| | Reagent | Mixing time (Min.) |
|---|---|---|
| 9. | DCC | — |
| 10. | Boc-amino acid | 50–90 |
| 11. | MeOH (twice) | 0.5 |
| 12. | $CH_2Cl_2$ (twice) | 0.5 |
| 13. | $Ac_2O$ (3M) in $CH_2Cl_2$ | 15.0 |
| 14. | $CH_2Cl_2$ | 0.5 |
| 15. | MeOH | 0.5 |
| 16. | $CH_2Cl_2$ (twice) | 0.5 |

Briefly, one to two mmol. of BOC-protected amino acid in methylene chloride is used per gram of resin, plus one equivalent of 1.0 molar DCC in methylene chloride for two hours. When BOC-Arg(Tos) is being coupled, a mixture of 50% DMF and methylene chloride is used. The amido group of Gln or Asn need not be protected (and was not in the present example) when DCC coupling is used in the presence of HOBt (e.g., 2 equivalents), but may be protected by Xan. P-nitrophenyl ester(ONp) may also be used to activate the carboxyl end of Gln or Asn, and for example, BOC-Gln(ONp) can be coupled overnight using one equivalent of HOBt in a 50% mixture of DMF and methylene chloride, in which case no DCC is added. Tos is used to protect the guanido group of Arg, and the indole nitrogen of Trp is left unprotected. The Asp and Glu side-chain carboxyl group is protected with OBzl. Bzl is used as the hydroxyl side-chain protecting group for Thr and Ser. 2-chloro-benzyloxycarbonyl (2 Cl-Z) is used as the protecting group for the side chain amino group of Lys. MeOBzl is used as a protecting group for the sulfhydryl group of Cys. The phenolic hydroxyl group of Tyr is protected with 2,6-dichlorobenzyl(DCB). The sulfur of Met is not oxidized.

With respect to the MCH, at the end of the synthesis the following composition is obtained: BOC-Asp(OBzl)-Phe-Asp(OBzl)-Met-Leu-Arg(Tos)-Cys(MeOBzl)-Met-Leu-Gly-Arg(Tos)-Val-Tyr(DCB)-Arg(Tos)-Pro-Cys(MeOBzl)-Trp-Gln-Val-O-$CH_2$-resin support.

In order to cleave and deprotect the protected peptide, the peptide-resin is treated with 1.5 ml. anisole, 0.5 ml. methylethylsulfide and 30 ml. hydrogen fluoride(HF) per gram of peptide-resin at 0° C. for about one and one-half hours. After elimination of the HF under high vacuum, the resin-peptide remainder is washed alternately with dry diethyl ether and ethyl acetate. The dry peptide and resin are then added to a solution of 8 liters of water, 2 liters of acetonitrile and 25 grams of ammonium acetate. The pH is adjusted to about 6.8 and air-oxidation of the peptide is carried out for about 4 days, with stirring, at room temperature (or until complete disappearance of —SH as measured by the Ellman test—see *Archives Biochem. Biophys.* 82, 1959, p. 70) to create a disulfide linkage between the two cysteine residues in each molecule. Filtration and concentration are then carried out through a plug of BioRex 70, and then the peptide is extracted with concentrated aqueous acetic acid.

Alternatively, it is possible to achieve the cysteine disulfide bond in higher yield by first reducing the cleaved and deprotected, linear peptide to its tetra S-sulfonate. Thereafter, following initial purification, the reduced peptide is converted to the cyclic form in the presence of a controlled amount of dithiothreitol.

The cleaved, deprotected and cyclic peptide is then concentrated on a suitable column, e.g., BioRex 70, from which it is eluted with 50% acetic acid and then frozen and lyophilized before being subjected to purification, which may include Sephadex G-50 fine gel filtration.

The peptide is purified by preparative or semi-preparative HPLC as described in Rivier et al., *J. of Chromatography*, 288, 303–328 (1984); Rivier et al., *Peptides: Structure and Biological Function*, (1979) pp 125–8; and Marki et al. *J. Am. Chem. Soc.* 103, 3178 (1981). Cartridges fitting Waters Associates prep LC-500 are packed with 15–20μ $C_{18}$ Silica from Vydac (300A). A gradient of $CH_3CN$ in TEAP 2.25 N. is generated by a low pressure Eldex gradient maker, as described in Rivier, J., *J. Lig. Chromatography*, 1, 343–367 (1978). The chromatographic fractions are carefully monitored by HPLC, and only the fractions showing substantial purity are pooled. Desalting of the purified fractions, independently checked for purity, is achieved using a gradient of $CH_3CN$ in 0.1% TFA. The center cut is then lyophilized to yield the desired peptide, the purity of which should be greater than 98%, based upon total weight of peptides. The peptide is judged to be homogeneous using thin layer chromatography with several different solvent systems. Amino acid analysis of the resultant, purified peptide is consistent with the sequence for the prepared structure. The optical rotation of the cyclic compound is measured at room temperature on a photoelectric polarimeter as $[\alpha]_D = -24.2°$ ±1° (c=0.483, 50% acetic acid).

EXAMPLE II

The synthesis of the NEI peptide having the formula:

Glu-Ile-Gly-Asp-Glu-Glu-Asn-Ser-Ala-Lys-Phe-Pro-Ile-$NH_2$, and the synthesis of the NGE peptides having the formula:

Gly-$X_{NGE}$-Phe-Pro-Ala-Glu-Asn-Gly-Val-Gln-Asn-Thr-Glu-Ser-Thr-Gln-Glu-OH, wherein $X_{NGE}$ is Pro-Ala-Val or Ser-Val-Ala, are carried out substantially as described in Example I, except that, in the synthesis of the NEI peptide, a MBHA resin support is used in place of the chloromethylated polystyrene resin.

At the end of the synthesis of NEI on the support, the protected peptide with the following formula is obtained:

BOC—Glu(OBzl)—Ile—Gly—Asp(OBzl)—Glu(OBzl)—Glu(OBzl)—Asn—
Ser(Bzl)—Ala—Lys(2 Cl—Z)—Phe—Pro—Ile—NH—CH-resin support.

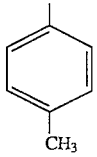

At the end of the synthesis of the NGEs on the support, the protected peptide with the following formula is obtained:

BOC-Gly-X"$_{NGE}$-Phe-Pro-Ala-Glu(OBzl)-Asn-Gly-Val-Gln-Asn-Thr(Bzl)-Glu(OBzl)-Ser(Bzl)-Thr(Bzl)-Gln-Glu(OBzl)-O-CH 2-resin support, wherein X"$_{NGE}$ is Pro-Ala-Val, if $X_{NGE}$ in the NGE is Pro-Ala-Val, or X"$_{NGE}$ is Ser(Bzl)-Val-Ala, if $X_{NGE}$ in the NGE is Ser-Val-Ala.

Each of the protected peptides is removed from the support and deprotected, and the deprotected peptide is isolated to at least about 98% of all protein present in the sample, following substantially the same procedures as described in Example I for the protected and deprotected MCH peptide.

The optical rotations of NEI and rat NGE were determined at room temperature on a photoelectric polarimeter to be as follows: For NEI, $[\alpha]_D=-50.8°$ (c=0.37, 50% acetic acid). For the NGE, $[\alpha]_D=-80.1°$ (c=0.73, 50% acetic acid).

EXAMPLE III

Salmon MCH, having the formula

H—Asp—Thr—Met—Arg—Cys—Met—Val—Gly—Arg—Val—Tyr—Arg—Pro—Cys—Trp—Glu—Val—OH is synthesized and purified as described in Example I. It is then conjugated to human alpha-globulins (U.S. Biochemicals, Frac IV) via glutaraldehyde by a reaction well known in the art. The salmon MCH-human alpha-globulins conjugate is diluted with physiological saline (0.9%s/v) to a final concentration of 1 mg total protein per milliliter Freund's Complete Adjuvant Modified M. butyricum (Calbiochem) is emulsified with an equal volume of saline containing either 1 mg conjugate/ml (for initial injections) or 0.5 mg conjugate/ml (for boosters). For each immunization, the rabbits receive a total of 1 ml emulsion in 20–30 intradermal sites; they are injected every 2 weeks and bled through an ear vein 7 days after each booster. Blood is allowed to clot, and serum is separated from cells by centrifugation. The antiserum from each bleeding is characterized with respect to titer and affinity. Some of this antiserum is labelled PBL #171.

Salmon MCH (1 μg) is radiolabelled using 1 mCurie $Na^{125}I$ (New England Nuclear, NEZ 033L) and 1 μg Chloramine T in a total volume of 40 μl of 1.25M sodium phosphate buffer, pH 7.5. Reaction is allowed to proceed for 30–45 seconds and then immediately quenched by the addition of 10 mg bovine serum albumin (BSA). $^{125}I$-salmon MCH is then purified by adsorption and elution from a BondElut C18 cartridge (Analytichem International). The eluant from the C18 cartridge is reduced to about 200 μl using a Savant Speed-Vac and then further purified by HPLC using a Vydac C18 column, 0.46×25 cm, 5 μm, 300 Å pore size. Buffer A is 0.1% trifluoroacetic acid (TFA); buffer B is 60% acetonitrile in 0.1% TFA. $^{125}I$-salmon MCH is loaded at 35% B at a flow rate of 1.5 ml/min, and a gradient is then run to 70% B in 40 minutes. Peak tubes of radioactivity are made 0.5% final in BSA. Several peaks of radioactivity are reproducibly eluted, and the first major zone of radioactivity is routinely used for the radioimmunoassay.

Throughout the purification, fractions are monitored using an RIA based upon this rabbit anti-salmon MCH antibody. Aliquots for assay are transferred into glass tubes containing BSA (10 μl of 10 mg/ml) and dried in a Savant Speed Vac. Fractions are resuspended in RIA assay buffer and pH checked and adjusted if necessary with NaOH. The radioimmunoassay is carried out using chilled reagents and with tubes partially immersed in ice water. On day one, 100 μl of buffer with Antibody PBL #171 1/24,000 dilution (1/120,000 final dilution) is added to glass tubes containing standard or test samples or buffer only in a volume of 300 μl. All treatments are tested in duplicate. Buffer is 0.1M sodium chloride, 0.05M sodium phosphate, 0.025M ethylenediaminetetraacetic acid (EDTA), 0.1% sodium azide, pH 7.5 (SPEA buffer) with 0.1% BSA. Standards ranging from 0.5 to 2000 pg of synthetic salmon MCH are used. Samples are tested at 2–5 dose levels. After these additions, tubes are vortexed and incubated at 4° C. for 24 hours. On day two, 20,000 cpm of $^{125}$-salmon MCH with 0.5% normal rabbit serum diluted in SPEA buffer +0.1% BSA is added in a volume of 100 μl to all tubes. The tubes are vortexed and returned to the cold for approximately 24 hours. On day three, tracer bound to antibody is precipitated with sheep anti-rabbit gamma globulins (100 μl, 1/40 dilution) and 0.5 ml of 10% (w/v) polyethylene glycol (SIGMA, MW=6,000 to 8,000). Tubes are vortexed and incubated 15 to 30 minutes at room temperature. Tubes are washed with 1 ml of SPEA buffer and centrifuged at 4° C. for 30–45 minutes at 2000× g. Supernatants are decanted, and pellets are counted in a gamma counter. Results are calculated using a standard logit/log radioimmunoassay data processing program NICHD RRB, NIH. The $EC_{50}$ and minimum detectable dose for salmon MCH are 18.5 ±3.2 pg (n=10) and 2.1 ±0.6 pg (n=10) respectively. The radioimmunoassay shows no cross-reactivity with α-MSH, β-MSH, rat ACTH, β-endorphin, arginine vasopressin, oxytocin, human GRF(1-40)-OH, rat GRF, rat CRF, GnRH, SS-14, or SS-28.

Several batches totaling approximately 60,000 lyophilized rat hypothalamic fragments are defatted by being ground in acetone, and the resulting powder is extracted with 10 volumes of a mixture of 90° C. 1N acetic acid (HAc), 0.1N HCl, 0.5% β-mercaptoethanol, 10 mM EDTA, and 5 μg/ml pepstatin A (Bachem). The hot slurry is immediately ground in a blender, cooled in an ice bath, and centrifuged. The supernatant is saved while the precipitate is re-extracted with the above mixture with the addition of 20 mM NaCl. The combined supernatants are defatted by multiple extraction with 3 volumes ether-petroleum ether (1:2). The aqueous phase from an individual batch of about 10,000 to 20,000 hypothalami equivalents is subjected to gel filtration chromatography at 4° C. using a Pharmacia K215/100 column packed with 85 cm Sephadex G-50 Fine, topped with 5 cm Sephades G-10, $V_t$=33 liters. It is eluted using 3N HAc with 0.2% β-mercaptoethanol at a flow rate of about 700 mls/hour. It appears to have about 2100 MW, based upon prior experience with this gel filtration system.

An affinity column is made using rabbit anti-salmon MCH-human alpha-globulins coupled directly to Protein A-Sepharose CL-4B (Pharmacia). Ten ml of antiserum PBL #171 is adsorbed with 100 mg of human alpha-globulins at 4° C. for 24 hours. The antiserum is spun down, and the pellet is discarded. The adsorbed antiserum is then rotated for 45 minutes at room temperature with a 10 ml bed volume amount of Protein A-Sepharose CL-4B, previously swollen and washed with 60 mls 50 mM NaHEPES, 150 mM NaCl, pH 7.5. The Protein A-Sepharose CL-4B beads are spun down, and the supernatant is removed. The beads are washed twice with 50 mM NaHEPES, 150 mM NaCl, pH 7.5 and twice with 0.2M triethanolamine-Cl, pH 8.2. The immunoglobulins bound to Protein A-Sepharose CL-4B are covalently cross-linked using dimethylpimelimidate dihydrochloride (DMPD, Pierce). The beads are resuspended in 20 volumes (200 mls) of 20 mM DMPD freshly made in 0.2M triethanolamine-Cl, pH 8.2 and rotated at room temperature for 60 minutes. The beads are centrifuged, the supernatant removed, and the reaction stopped by resuspending the beads in 20 volumes (200 mls) of 0.02M ethanolamine-Cl, pH 8.2. The antibody-Protein A beads are then washed twice with 1N HAc and equilibrated with 50 mM Na HEPES, 150 mM NaCl, pH 7.5. The coupling efficiency of the rabbit anti-salmon MCH fraction to Protein A-Sepharose CL-4B is about 90%.

The active zones from Sephadex G-50 sizing of several batches of rat hypothalami are pooled, lyophilized, reconstituted in 500 mls of 50 mM NaHEPES, pH 7.5 and filtered through a 0.45 μm filter (Millipore). After rotating with the immunoaffinity chromatography matrix for 48 hours at 4° C., the mixture is packed into a 1.5×10 cm column (BioRad) at 25 ml/hr. The column is washed with 50 mM NaHEPES, pH 7.5, and the bound material is then eluted with 1N HAc at 25 ml/hr.

Active fractions from the immunoaffinity column are pooled, lyophilized and resuspended in 1 ml 4M Guanidine HCl, 0.5N HAc. They are further purified in 2 batches using an FPLC system (Pharmacia) equipped with tandem Superose 12B columns, 10 μm, 10×300 mm each, using an eluant of 1N HAc and a flow rate of 0.4 ml/hr. The active fractions are again identified using the RIA.

The active fractions from this gel filtration are pooled, concentrated to 0.1 ml in a Savant Speed Vac system, and final purification is effected using two steps of narrow bore reversed phase HPLC. A Vydac C18 column, 2.1×150 mm, 5 μm particle size, 300 Å pore size, is used at a flow rate of 0.25 ml/min. Buffer A is 0.05% aqueous trifluoroacetic acid (TFA); buffer B is 90% acetonitrile, 0.05% TFA. The sample is loaded at 0% B for 5 min, a gradient run to 50% B in 40 min, followed by isocratic elution at 50% B for 5 min. Fractions are collected manually based on UV absorption at 210 nm. Aliquots of these fractions are assayed in the sMCH radioimmunoassay, and the zones found to be immunoreactive are collected, pooled and subsequently concentrated to dryness in a Savant Speed Vac system. The sample is redissolved immediately in 0.5M acetic acid and applied to a narrow bore reversed-phase column (Vydac C18; 2.1× 1.50 mm; particle size, 5 μm; pore size 300 Å) and eluted at a flow rate of 0.125 ml/min with a mixture of 0.05% aqueous TFA and acetonitrile (linear gradient from 0% to 36% acetonitrile in 90 min). Fractions are collected manually based on the absorption at 210 nm. Aliquots are assayed for MCH-like immunoreactivity.

The several fractions exhibiting the highest immunoreactivity are each subjected separately to Edman degradation in a gas phase protein sequencer (Applied Biosystems 470 A). The phenylthiohydantoin derivatives of the amino acids are identified by reversed phase HPLC as well known in the art. The following peptide sequence is obtained for some of the fractions: Asp-Phe-Asp-Met-Leu-Arg-Cys-Met-Leu-Gly-Arg-Val-Tyr-Arg-Pro-Cys-Trp-Glx-Val. It was not possible to determine if position-18 is glutamine or glutamic acid, nor whether the C-terminus is amidated. However, reduction of the remaining fractions with dithiothreitol and then reaction with 4-vinyl pyridine, followed by purification using narrow bore HPLC and then sequencing, confirmed the existence of cystsine residues in positions 7 and 16.

EXAMPLE IV

Approximately 5×10⁵ independent recombinants from a rat hypothalamic cDNA library in λZAP (Stratagene Cloning Systems, La Jolla, Calif., USA) were screened for the MCH sequence using an oligoprobe having the nucleotide sequence: 5'-GCCCAGCATGCACCGCAGCATGT-CAAAGTC, deduced, following Lathe, J. Mol. Biol. 183, 1–12 (1985), from the sequence of the N-terminal ten amino acids of mature MCH of rat. Four hybridization positive clones were found, and these were then fully characterized by the combination of restriction enzyme mapping and sequencing analysis. It was found that all these clones code for an identical polypeptide which is believed to be the precursor of rat MCH. The results of this sequencing are set forth in Table 1 hereinafter.

The biologically active rat MCH peptide is located at the carboxy-terminus of this precursor (encoded by the nucleotides in positions 466 to 522) and is preceded by a potential dipeptide cleavage site (Arg-Arg) and is followed by a stop codon (TGA). The 19 amino acid sequence which is deduced for mature MCH from the cDNA sequence confirms the peptide sequence, which was established by chemical analysis and upon which the probe sequence was based.

It is believed that one or more biologically active peptides may be present in the precursor N-terminally of rat MCH. One of these peptides is the 13-residue peptide amide NEI, of sequence Glu-Ile-Gly-Asp-Glu-Glu- Asn-Ser-Ala-Lys-Phe-Pro-Ile-NH₂. The peptidylglycine precursor of NEI is encoded by the nucleotide sequence between positions 418 and 459, inclusive, in the sequence of Table 1. NEI is then made from the MCH precursor by proteolytic processing between the dipeptide Lys-Arg, encoded by nucleotides 412–417 in the sequence in Table 1, and the amino acid Glu, which is at the N-terminus of NEI, proteolytic processing between the dipeptide Arg-Arg, encoded by nucleotides 460–465 in the sequence of Table 1, and the amino acid Gly, which is at the carboxy-terminus of the peptidylglycine precursor of NEI, and deglyoxylation to convert the peptidylglycine precursor to the peptidylamide, NEI. Another of these peptides is rat NGE, of sequence Gly-Pro-Ala-Val-Phe-Pro-Ala-Glu-Asn-Gly-Val-Gln-Asn-Thr-Glu-Ser-Thr-Gln-Glu-OH. NGE is encoded by the nucleotide sequence between positions 355 and 411, inclusive, in the sequence of Table 1. NGE is then made from the MCH precursor by proteolytic processing between the amino acid Lys, encoded by nucleotides 351–354 in the sequence of Table 1, and the Gly, which is at the N-terminus of NGE, and proteolytic processing between the dipeptide Lys-Arg, encoded by nucleotides 412–417 in the sequence in Table 1, and the Glu, which is at the carboxy terminus of NGE.

sequences of all mammalian MCHs are highly conserved and, therefore, closely similar, the sequence of human MCH is identical to that of rat MCH and the nucleotide sequences

TABLE 1

```
              10              20                    30         39            48              57
CTTCGGCTTT  ACGGAGCAGC    AAACAGG  ATG GCG AAG  ATG AGC CTC  TCT TCC TAC  ATG
                                   MET Ala Lys  MET Ser Leu  Ser Ser Tyr  MET 66              75              84           93           102            111
TTA ATG CTG GCC TTT TCT TTG TTT TCT CAC CGC ATT TTA CTT TCG GCC TCC AAG
Leu MET Leu Ala Phe Ser Leu Phe Ser His Gly Ile Leu Leu Ser Ala Ser Lys 120             129             138          147          156            165
TCC ATC AGG AAC GTA GAA GAC GAC ATA GTA TTT AAT ACA TTC AGG ATG GGG AAA
Ser Ile Arg Asn Val Glu Asp Asp Ile Val Phe Asn Thr Phe Arg MET Gly Lys 174             183             192          201          210            219
GCC TTT CAG AAG GAA GAT ACC GCA GAA AGA TCG GTT GTT GCT CCT TCT CTG GAA
Ala Phe Gln Lys Glu Asp Thr Ala Glu Arg Ser Val Val Ala Pro Ser Leu Glu 228             237             246          255          264            273
GGA TAC AAA AAT GAT GAG AGC GGC TTC ATG AAG GAT GAC GAT GAC AAG ACC ACA
Gly Tyr Lys Asn Asp Glu Ser Gly Phe MET Lys Asp Asp Asp Asp Lys Thr Thr 282             291             300          309          318            327
AAG AAC ACA GGC TCC AAG CAG AAT CTC GTA ACT CAC GGT CTG CCC CTC AGT CTG
Lys Asn Thr Gly Ser Lys Gln Asn Leu Val Thr His Gly Leu Pro Leu Ser Leu 336             345             354          363          372            381
GCT GTA AAA CCT TAC CTC GCT CTG AAA GGA CCA GCA GTC TTC CCA GCT GAG AAT
Ala Val Lys Pro Tyr Leu Ala Leu Lys Gly Pro Ala Val Phe Pro Ala Glu Asn 390             399             408          417          426            435
GGA GTT CAG AAT ACT GAG TCC ACA CAG GAA AAG AGG GAA ATT GGG GAT GAA GAA
Gly Val Gln Asn Thr Glu Ser Thr Gln Glu Lys Arg Glu Ile Gly Asp Glu Glu 444             453             462          471          480            489
AAC TCA GCT AAA TTT CCC ATA GGA AGG AGA GAT TTT GAC ATG CTC AGG TGT ATG
Asn Ser Ala Lys Phe Pro Ile Gly Arg Arg Asp Phe Asp MET Leu Arg Cys MET 498             507             516          532          542            552
CTG GGA CGA GTC TAC CGA CCC TGT TGG CAA GTC  TGATACCTGC  TGGTCCACAA  CATCCTTTCA
Leu Gly Arg Val Tyr Arg Pro Cys Trp Gln Val 562             572             582          592          602          612          622
   GAAGAAAACG  ATTCATTGCA AGTGGAGAGA  AAAGCCCTTA  ATGTTGATGT  AACTTGTGTA  TCATCCTAAA 632             642             652          662          672          682          692
   TGTCTGTTTT  AAAAGAAACT GGTTACAATA  TGTAAATGCT  ATGTAAATGA  TATGCTTTGA  CTTGTGCATT 702             712
```

EXAMPLE V

Following substantially the procedure described in Example IV with a human hypothalamic cDNA library in λgt11 and the probe 5'-CCAACAGGGTCGGTA-GACTCGTCCCAGCAT, which has the sequence complementary to that of the segment between and including positions 487–516 specified in Table 1, the sequence of the cDNA encoding the putative human MCH precursor and the amino acid sequence of said precursor deduced from said cDNA sequence were determined. These sequences are provided below in Table 2, with reference to the rat cDNA and amino acid sequences in Table 1.

The human MCH precursor has the same number of amino acids as the rat MCH precursor.

As in the rat precursor, the mature human MCH occurs as the carboxy-terminal 19 amino acids, preceded by the dipeptide Arg-Arg, which presumably serves as a diaminopeptidase cleavage site in the in vivo processing of the precursor to provide the mature MCH. Supportive of the view that the of the cDNA segments encoding the two mature MCHs and the Arg-Arg dipeptide at the amino-termini thereof differ at only 3 of 63 positions.

Further, the human MCH precursor includes an NEI peptide, of sequence identical to that of the rat NEI and, the same as in the rat precursor, preceded at the amino-terminus by the dipeptide Lys-Arg, which presumably serves as a cleavage site for a diaminopeptidase in the in vivo processing of the precursor to yield NEI, and having an amide at the carboxy-terminus resulting from processing of the glycine coded in the cDNA at the carboxy-terminus. The nucleotide sequences of the cDNA segments encoding the human and rat NEIs, including the Gly at the carboxy-termini and the Lys-Arg dipeptide at the amino-termini thereof, differ at only 2 of 48 positions. As with MCH, the identity of the human and rat NEI amino acid sequences and the high degree of homology in the cDNA segments encoding them support the view that all mammalian NEIs have closely similar sequences.

Still further, the human MCH precursor includes an NGE peptide, which is highly homologous in sequence to that of rat NGE, differing from the rat only in having Ser-Val-Ala in place of Pro-Ala-Val as residues 2–4, and which, like in rat, is preceded at the amino-terminus by a Lys, which may serve as a proteolytic processing site for the production in vivo of the NGE from the human MCH precursor. In view of the homology, in the amino acid sequences of human and rat NGEs together with the Lys residues immediately preceding the N-termini thereof in the human and rat MCH precursors, and in the nucleotide sequences of the cDNAs encoding these amino acid sequences (differing at only 8 of 60 positions), it is likely that the amino acid sequences of the NGEs of all mammmalian species are closely similar.

TABLE 2

757 base pairs of a cDNA comprising a segment encoding the human MCH precursor were sequenced. Except as indicated as follows, of the 757 sequenced base pairs, the 498[1] that code for the human MCH precursor, including the ATG, which encodes the translational start signal in the mRNA for said precursor, and the TGA, which encodes the translational stop signal in the mRNA for said precursor, have the same sequence as the 498 base pairs indicated in Table 1 that code for the rat MCH precursor, including the ATG encoding the translational start signal and the TGA encoding the translational stop signal:

| Position[2] in Rat MCH Precursor cDNA for Which Base Differs at Corresponding Position in Human MCH Precursor cDNA | Base in Human MCH Precursor cDNA at Position Indicated in Column 1 | Amino Acid Change Due to Base Change Indicated in Column 2? | Amino Acid Change from Rat to Human Precursor[3] |
|---|---|---|---|
| 33  | A | No  | — |
| 36  | A | No  | — |
| 41  | A | Yes | Ser to Asn |
| 42  | T | Yes | " |
| 54  | T | No  | — |
| 57  | A | Yes | Met to Ile |
| 63  | A | Yes | Met to Ile |
| 66  | A | No  | — |
| 67  | A | Yes | Ala to Thr |
| 69  | T | Yes | " |
| 87  | A | Yes | His to Gln |
| 90  | T | No  | — |
| 102 | A | No  | — |
| 105 | A | No  | — |
| 117 | A | No  | — |
| 120 | A | No  | — |
| 123 | T | No  | — |
| 124 | T | Yes | Val to Leu |
| 129 | T | Yes | Glu to Asp |
| 132 | T | No  | — |
| 138 | G | Yes | Ile to Met |
| 157 | T | Yes | Met to Leu |
| 167 | G | Yes | Ala to Gly |
| 183 | C | No  | — |
| 186 | T | No  | — |
| 194 | A | Yes | Arg to Lys |
| 198 | A | No  | — |
| 202 | A | Yes | Val to Ile |
| 213 | C | No  | — |
| 220 | C | Yes | Gly to Gln |
| 221 | A | Yes | " |
| 225 | T | No  | — |
| 241 | A | No  | — |
| 243 | T | No  | — |
| 252 | C | Yes | Lys to Asn |
| 255 | A | Yes | Asp to Glu |
| 258 | G | Yes | Asp to Glu |
| 261 | A | Yes | Asp to Glu |
| 262 | A | Yes | Asp to Asn |
| 264 | T | Yes | " |

TABLE 2-continued 757 base pairs of a cDNA comprising a segment encoding the human MCH precursor were sequenced. Except as indicated as follows, of the 757 sequenced base pairs, the 498[1] that code for the human MCH precursor, including the ATG, which encodes the translational start signal in the mRNA for said precursor, and the TGA, which encodes the translational stop signal in the mRNA for said precursor, have the same sequence as the 498 base pairs indicated in Table 1 that code for the rat MCH precursor, including the ATG encoding the translational start signal and the TGA encoding the translational stop signal:

| Position[2] in Rat MCH Precursor cDNA for Which Base Differs at Corresponding Position in Human MCH Precursor cDNA | Base in Human MCH Precursor cDNA at Position Indicated in Column 1 | Amino Acid Change Due to Base Change Indicated in Column 2? | Amino Acid Change from Rat to Human Precursor[3] |
|---|---|---|---|
| 267 | A | No  | — |
| 268 | G | Yes | Thr to Val |
| 269 | T | Yes | " |
| 270 | T | Yes | " |
| 271 | T | Yes | Thr to Ser |
| 291 | A | No  | — |
| 294 | T | Yes | Gln to His |
| 298 | T | Yes | Leu to Phe |
| 301 | T | Yes | Val to Leu |
| 305 | A | Yes | Thr to Asn |
| 309 | T | No  | — |
| 318 | A | No  | — |
| 321 | G | No  | — |
| 323 | A | Yes | Ser to Asn |
| 331 | A | Yes | Val to Ile |
| 342 | T | No  | — |
| 345 | T | No  | — |
| 348 | A | No  | — |
| 351 | A | No  | — |
| 358 | T | Yes | Pro to Ser |
| 360 | T | Yes | " |
| 362 | T | Yes | Ala to Val |
| 365 | c | Yes | Val to Ala |
| 366 | T | Yes | " |
| 399 | A | No  | — |
| 402 | A | No  | — |
| 408 | A | No  | — |
| 417 | A | No  | — |
| 453 | T | No  | — |
| 483 | A | No  | — |
| 496 | A | No  | — |
| 510 | T | No  | — |

[1]Of the 757 sequenced base pairs, the 57 that are upstream of the ATG, which encodes the translational start signal in the mRNA for the human MCH precursor, have the sequence 5'-TTCCGAGAAA TTTTTCATTT CTTTCT-TGTT TGACTGTATG CAAACATCAA ACTAAGA and the 202 that are downstream of the TGA, which encodes the translational stop signal in the mRNA for the human MCH precursor, have the sequence: 5'-TACCTGTTGG TCCACATCAT CTTTTCAGAA GAAAATAAAA GCATTTAATT GCCAATGGGA GGAGAAGCCC ATACTGCTAC TATAACTTGT GTAT-GTTAAGA TGTCTGTTTT AAAAGAAAGT AGTGTTAAGA TGTAT-CAGTA ACTGAAATGA TATGCTTTCT CTGTGCATTA AACTTTGTGA AAATTCTGCA TAAAAAAAAA AA.
[2]As indicated in Table 1.
[3]A ditto mark, ", indicates that the nucleotide change is in the same triplet of bases that encodes the amino acid indicated immediately above.

EXAMPLE VI

Whereas the salmon MCH shows extremely little biological potency in mammalian assays, the mammalian MCH peptide shows more potent reaction than the alpha-MSH and beta-MSH antagonists that have been known for some time.

The synthetic MCH peptide prepared in Example I shows displacement in radioimmunoassays which are also run with synthetic salmon MCH. In vitro assays are performed with the mammalian MCH and the synthetic salmon MCH peptides, using rat pituitary halves to monitor for the secretion of ACTH. Assays of this type are described in more detail in *Proc. Natl. Acad. Sci.*, 85, 5556–5560 (1988). The results of this in vitro testing shows that the MCH peptides produced in the examples are very potent modulators of ACTH production, whereas salmon MCH exhibits substantially no effect on the secretion of ACTH in such a rat pituitary assay. As a result, it is believed that mammalian MCH should be useful as a natural, peptide regulator of the pituitary-adrenal axis. It is likewise believed that mammalian MCH peptides will be useful for clinical application in the treatment of pigment disorders as well as in the diagnosis and therapy of melanoma. It is also believed that they will be effective in the treatment of certain forms of dementia and may have uses in connection with nerve damage situations.

When a physician wishes to modulate ACTH secretion in human clinical applications using such MCH peptides, dosages between about 100 nanograms and about 50 micrograms of these peptides per kilogram of body weight are considered to be effective and will likely be employed by physicians for this purpose. On the other hand, treatments of pigment disorders and/or melanoma may be treated topically. Physicians making such treatments may employ suitable concentrations of the peptide for the topical application, and, in this respect, could rely upon data generated in connection with the use of MSH (melanin stimulating hormone) antagonists for this purpose.

Such peptides are often administered in the form of pharmaceutically or veterinarily acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

It may also be desirable to deliver MCH over prolonged periods of time, for example, for periods of one week to one year from a single administration, and slow release, depot or implant dosage forms may be utilized. For example, a dosage form may contain a pharmaceutically acceptable non-toxic salt of the compound which has a low degree of solubility in body fluids, for example, an acid addition salt with the polybasic acid; a salt with a polyvalent metal cation; or combination of the two salts. A relatively insoluble salt may also be formulated in a gel, for example, an aluminum stearate gel. A suitable slow release depot formulation for injection may also contain MCH or a salt thereof dispersed or encapsulated in a slow degrading, non-toxic or non-antigenic polymer such as a polylactic acid/polyglycolic acid polymer, for example, as described in U.S. Pat. No. 3,773,919. It may also be feasible to incorporate such a compound in a silastic implant.

The peptides should be administered under the guidance of a physician, and pharmaceutical compositions will usually contain the peptide in conjunction with a conventional, pharmaceutically or veterinarily-acceptable carrier. Depending upon the condition being treated, system dosages may be used in the range of from about 0.01 to about 10 milligrams of the peptide per kilogram of the body weight of the host animal.

As used herein, all temperatures are in °C. and all ratios are by volume. Percentages of liquid materials are also by volume. For all polypeptides and fragments thereof, the sequence is written from the amino-terminal amino acid, which is specified first, to the carboxy-terminal amino acid (or amide), which is specified last.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at various positions in the MCH, NEI and NGE peptide chains can be made in accordance with present or future developments without detracting from the potency or utility thereof. For instance, instead of the free acid at the C-terminus of MCH or NGE, it may be suitable to utilize a simple amide, or a lower alkyl-substituted amide, e.g. with 1–4 carbon atoms in the alkyl group, such as methylamide, ethylamide, etc. Such peptides are considered as being within the scope of the invention.

Various features of the invention are emphasized in the claims which follow.

What is claimed is:

1. A peptide with a sequence selected from the group consisting of H-Glu-Ile-Gly-Asp-Glu-Glu-Asn-Ser-Ala-Lys-Phe-Pro-Ile-NH$_2$ and H-Gly-X$_{NGE}$-Phe-Pro-Ala-Glu-Asn-Gly-Val-Gln-Asn-Thr-Glu-Ser-Thr-Gln-Glu-Y, wherein X$_{NGE}$ is Pro-Ala-Val or Ser-Val-Ala and Y is OH or NH$_2$.

2. A peptide according to claim 1 with the sequence H-Glu-Ile-Gly-Asp-Glu-Glu-Asn-Ser-Ala-Lys-Phe-Pro-Ile-NH$_2$.

3. A peptide according to claim 1 with the sequence H-Gly-Pro-Ala-Val-Phe-Pro-Ala-Glu-Asn-Gly-Val-Gln-Asn-Thr-Glu-Ser-Thr-Gln-Glu-OH.

4. A peptide according to claim 1 with the sequence H-Gly-Ser-Val-Ala-Phe-Pro-Ala-Glu-Asn-Gly-Val-Gln-Asn-Thr-Glu-Ser-Thr-Gln-Glu-OH.

* * * * *

UNITED STATES PATENT AND TRADEMARK OFFICE
CERTIFICATE OF CORRECTION

PATENT NO. : 5,530,095
DATED : June 25, 1996
INVENTOR(S) : Vaughan, et al.

It is certified that error appears in the above-indentified patent and that said Letters Patent is hereby corrected as shown below:

ON THE TITLE SHEET:

Item [19], change "Vaughn et al." to -- Vaughan et al.--

In [75], change "Joan Vaughn" to --Joan Vaughan--.

Signed and Sealed this

Fifth Day of November, 1996

Attest:

BRUCE LEHMAN

*Attesting Officer*     *Commissioner of Patents and Trademarks*